United States Patent [19]

Mandeville, III et al.

[11] Patent Number: 5,487,888
[45] Date of Patent: Jan. 30, 1996

[54] IRON-BINDING POLYMERS FOR ORAL ADMINISTRATION

[75] Inventors: W. Harry Mandeville, III, Lynnfield; Stephen R. Holmes-Farley, Arlington, all of Mass.

[73] Assignee: GelTex, Inc., Waltham, Mass.

[21] Appl. No.: 65,546

[22] Filed: May 20, 1993

[51] Int. Cl.$^6$ .................................................. A61K 31/785
[52] U.S. Cl. .................. 424/78.1; 424/78.01; 424/78.12; 424/78.37
[58] Field of Search .................. 424/78.01, 78.1, 424/78.37, 78.12

[56] References Cited

U.S. PATENT DOCUMENTS

| | | | |
|---|---|---|---|
| 5,114,709 | 5/1992 | St. Pierre et al. | 424/78.12 |
| 5,236,701 | 8/1993 | St. Pierre et al. | 424/78.12 |

FOREIGN PATENT DOCUMENTS

| | | | |
|---|---|---|---|
| 0162388 | 11/1985 | European Pat. Off. | 424/78.1 |
| 865836 | 4/1961 | United Kingdom . | |

OTHER PUBLICATIONS

Bhaduri et al., ":3–Methylenepentage–2,4–dionated Polystyrene as Polydentate Ligand for Transition Metal Ions" J. Indian Chem. Soc. A19:362–363 (1980).
Bottino et al. "Metal Selectivity Properties of Polymeric Schiff Bases" Inorg. Nucl. Chem. Letters 16:417–421 (1980).
Furue et al. "Preparation of Poly(vinyl–2,2'–Bipyridine) and Complex Formation with Various Metal Ions" J. Of Polymer Science: Polymer Letters Edition 20:291–295 (1982).
Ghosh et al. "Preparation and Properties of a new chelating resin containing 1–nitroso–2–naphthol as the functional group" Talanta 28:274–276 (1981).
Hodgkin et al. "Use of $^{13}$C–NMR in the study of reactions on crosslinked resins" J. of Polymer Science 19:1239–1249 (1981).
Lee et al. "The use of a chelating resin column for preconcentration of trace elements from sea–water in their determination by neutron–activation analysis" Talanta 24:241–245 (1977).
Melby "Polymers for selective chelation of transition metal ions" J. of Am. Chem. Society 97:4045–4051 (1975).
Patel et al. "Preparation and chelating properties of 4–Bromosalicyclic acid–formaldehyde polymers" J. Macromol. Sci.–chem. a17:1383–1398 (1982).
Warshawsky et al. "Functionalization of polystyrene. 1.alkylation with substituted benzyl halide and benzyl halide and benzyl alcohol compounds" J. Org. Chem. 43:3151–3157 (1978).
Warshawsky et al. "Polymeric pseudocrown ethers. 1. Synthesis and complexation with transition metal anions" J. of Am. Chem. Society 101:4249–4258 (1979).
Warshawsky "Chelating ion exchangers" Ion Exchange and Sorption Processes in Hydrometallurgy Critical Reports on Applied Chemistry J. Wiley & Sons 15:166–226 (1987).
Winston et al. "Hydroxamic acid polymers. Effect of structure on the selective chelation of iron in water" Hydroxamic Acid Polymers 11:597–603 (1978).
Winston et al. "Hydroxamic acid polymers II. Design of a polymeric chelating agent for Iron" J. of Polymer Science 14:2155–2165 (1976).
Edwards et al. "Screening for Hemochromatosis" NEJ of Medicine 328:1616–1620 (Jun. 1993).
Winston et al., "Functional Polymers for Removal of Heavy–Metal Pollutants from Water" Water Research Inst. Technical Project: A–031–WVA (1980).

*Primary Examiner*—Thurman K. Page
*Attorney, Agent, or Firm*—Hamilton, Brook, Smith & Reynolds

[57] ABSTRACT

Iron binding polymers are provided for decreasing the absorption of iron from the gastrointestinal tract. The polymers are orally administered, and are useful for treatment of iron overload disorders.

19 Claims, No Drawings

IRON-BINDING POLYMERS FOR ORAL ADMINISTRATION

BACKGROUND OF THE INVENTION

This invention relates to iron-binding polymers, particularly polymers administered orally to decrease the absorption of dietary iron from the gastrointestinal tract.

Reduced uptake of dietary iron is clinically important in several related metabolic disorders. In patients with hemachromatosis too much dietary iron is absorbed and patients experience iron overload. Genetic hemachromatosis is due to a somatic gene mutation. While tissue damage is greatest in individuals who are homozygous for the defective gene, reduction of iron uptake is also desirable in patients who are heterozygous for the implicated mutation (Finch et al., *N. Engl. J. Med.*, 306:1520, 1982). Acquired hemachromatosis includes conditions characterized by tissue injury associated with iron overload, where disease processes other than genetic mutations cause the exacerbated iron uptake. Examples of such diseases include iron-loading anemias, such as thalassemia and sideroblastic anemia, as well as certain types of liver dysfunction (Finch et al., *N. Engl. J. Med.*, 306: 1520, 1982). The massive deposits of iron in body tissues cause similar organ failure in both genetic and acquired hemachromatosis.

Until recently, relatively high iron levels were considered desirable in all individuals. However, increased rates of heart disease are now known to be associated with elevated serum ferritin levels (an indicator of the body burden of iron). In the heterozygous state of hemachromatosis, for example, the degree of iron overload is not sufficient to lead to the traditional symptoms of overload, including abdominal pain, hepatomegaly, diabetes, impotence, and gray pigmentation of the skin. The iron overload may be sufficient, however, to lead to increased probability of heart disease such as congestive heart failure.

A typical adult man has 4–6 g of iron in his body, and absorbs approximately 1 mg of the 10–20 mg of iron available from his daily diet. Iron is absorbed in two basic forms, free iron and heme-bound iron. Free iron can be in either the ferrous ($Fe^{+2}$) or ferric ($Fe^{+3}$) forms, and can be complexed to various organic and inorganic dietary ingredients (such as phosphate, phytate and citrate). The two forms of free iron are absorbed equally well provided that they both remain in an ionized form, and not in the easily formed and insoluble hydroxides. A typical adult diet contains approximately 1.6 mg of heme-bound iron and 13 mg of free iron. Heme-bound iron, while present in smaller amounts in the diet than free iron, is more readily absorbed than free iron. Approximately 23% of heme-bound iron is available for absorption, while the absorbable fraction of dietary free iron ranges from 3–8%, depending on the other constituents of the diet. The result of these factors is that both heme-bound and free iron contribute significantly to dietary iron uptake.

Iron is absorbed primarily in the proximal segments of the small intestine. It is absorbed by the mucosal cells, processed into appropriate forms, and released into the plasma.

SUMMARY OF THE INVENTION

In general, the invention features a method of reducing dietary iron absorption in a patient which involves oral administration of a therapeutically effective amount of one or more iron-binding polymers that are non-toxic and stable once ingested.

By "non-toxic" it is meant that when ingested in therapeutically effective amounts neither the polymers nor any ions released into the body upon ion exchange are harmful.

By "stable" it is meant that when ingested in therapeutically effective amounts the polymers do not dissolve or otherwise decompose to form potentially harmful by-products, and remain substantially intact so that they can transport bound iron out of the body.

In a preferred embodiment, a polymer of the method of the invention reduces dietary iron absorption by at least about 70%, and more preferably by at least about 95%. In another preferred embodiment, the polymer reduces absorption of dietary heme iron by at least about 70%. In a further preferred embodiment, the polymer reduces absorption of dietary free iron by at least about 70%.

In one preferred embodiment the polymer includes primary, secondary, tertiary, or quaternary amines. These amines may include —$NR_3^+$, where each R group, independently, is H or a lower alkyl or aryl group.

In another preferred embodiment, the polymer includes iron chelating groups, which may include a phenolate, enolic hydroxyl, ketone, aldehyde, carboxylate, phosphate, phosphonate, thiolate, sulfide, disulfide, hydroxamic acid, hydroxamate, amine, amide, nitrone, ether, thiol, hydroxyl, sulfonate, nitrile, or isonitrile group, or combination thereof.

The polymers of the invention may be crosslinked.

One example of a preferred polymer is characterized by a repeating group having the formula

or a copolymer thereof, wherein n is an integer, and each R, independently, is H, OH, or a lower alkyl or aryl group.

A second example of a preferred polymer is characterized by a repeating group having the formula

or a copolymer thereof, wherein n is an integer, each R, independently, is H, OH, or a lower alkyl or aryl group, and each $M^-$ is an exchangeable negatively charged counterion.

A third example of a preferred polymer is characterized by a repeating group having the formula

or a copolymer thereof, wherein n is an integer, and each $R_1$ and $R_2$, independently, is H, OH, or a lower alkyl or aryl group, and each $M^-$ is an exchangeable negatively charged counterion.

A fourth example of a preferred polymer is characterized by a repeating group having the formula

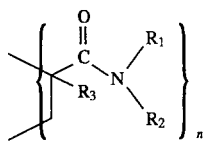 (4)

or a copolymer thereof, wherein n is an integer, $R_3$ is either H or a lower alkyl, and each $R_1$ and $R_2$, independently, is H, OH, a lower alkyl or aryl group, or $(CH_2CH_2NH)_mH$, wherein m is an integer from 1 to 10,000.

A fifth example of a preferred polymer is characterized by a repeating group having the formula

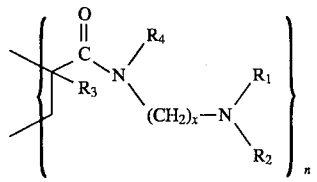 (5)

or a copolymer thereof, wherein n is an integer, $R_3$ is either H or a lower alkyl group, each $R_1$, $R_2$, and $R_4$, independently, is H, OH, or a lower alkyl or aryl group, and x is an integer from 1 to 25.

A sixth example of a preferred polymer is characterized by a repeating group having the formula

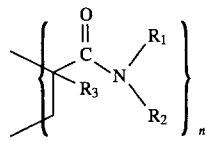 (6)

or a copolymer thereof, wherein n is an integer, $R_3$ is either H or a lower alkyl group, each $R_1$ and $R_2$, independently, is H, OH, a lower alkyl or aryl group, or an iron binding ligand. Said iron binding ligands are organic moieties which include one or more functional groups capable of complexing with iron. Such complexing groups include phenolate, enolic hydroxyl, ketone, aldehyde, carboxylate, phosphate, phosphonate, thiolate, sulfide, disulfide, hydroxamic acid, hydroxamate, amine, amide, nitrone, ether, thiol, hydroxyl, sulfonate, nitrile, isonitrile, or combination thereof.

A seventh example of a preferred polymer is characterized by a repeating group having the formula

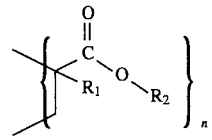 (7)

or a copolymer thereof, wherein n is an integer, $R_1$ is either H or a lower alkyl or aryl group, $R_2$ is H, OH, a lower alkyl group, or an iron binding ligand. Said iron binding ligands are organic moieties which include one or more functional groups capable of complexing with iron. Such complexing groups include phenolate, enolic hydroxyl, ketone, aldehyde, carboxylate, phosphate, phosphonate, thiolate, sulfide, disulfide, hydroxamic acid, hydroxamate, amine, amide, nitrone, ether, thiol, hydroxyl, sulfonate, nitrile, isonitrile, or combination thereof.

An eighth example of a preferred polymer is characterized by a repeating group having the formula

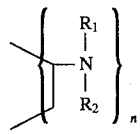 (8)

or a copolymer thereof, wherein n is an integer, each $R_1$ and $R_2$, independently, is H, an alkyl group containing 1 to 20 carbon atoms, or an aryl group containing 1 to 12 atoms. A specific example is poly(vinylamine).

A ninth example of a preferred polymer is characterized by a repeating group having the formula

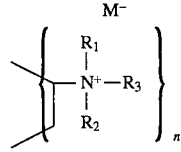 (9)

or a copolymer thereof, wherein n is an integer, each $R_1$, $R_2$ and $R_3$, independently, is H, an alkyl group containing 1 to 20 carbon atoms, or an aryl group containing 1 to 12 atoms, and each $M^-$ is an exchangeable negatively charged counterion. A specific example is poly(trimethylammonium bromide).

In another aspect, the invention features a therapeutic composition suitable for oral administration, including a therapeutically effective amount of at least one polymer that binds dietary iron, where the polymer is non-toxic and stable once ingested. By "therapeutically effective" is meant a composition which, when administered to a patient causes decreased absorption of dietary iron.

The invention provides an effective treatment for decreasing the absorption of dietary iron, and thereby reducing the patient's total body iron stores. The compositions are non-toxic and stable when ingested in therapeutically effective amounts.

Other features and advantages will be apparent from the following description of the preferred embodiments and from the claims.

DESCRIPTION OF THE PREFERRED EMBODIMENTS

The polymers are preferably crosslinked, in some cases by adding a crosslinking co-monomer to the reaction mixture during polymerization. Examples of suitable crosslinking co-monomers are diacrylates and dimethacrylates (e.g., ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate, polyethyleneglycol diacrylate), methylene bisacrylamide, methylene bismethacrylamide, ethylene bisacrylamide, ethylenebismethacrylamide, ethylidene bisacrylamide, divinyl benzene, bisphenol A dimethacrylate, and bisphenol A diacrylate. The amount of crosslinking co-monomer is typically between 1.0 and 25 weight %, based upon combined weight of crosslinking agent and monomer.

In some cases the polymers are crosslinked after polymerization. One method of obtaining such crosslinking involves reaction of the polymer with difunctional crosslinkers, such as epichlorohydrin, succinyl dichloride, the diglycidal ether of bisphenol A, pyromellitic dianhydride, toluene diisocyanate, and ethylenediamine. A typical example is the reaction of poly(ethyleneimine) with epichlorohydrin. In this example the epichlorohydrin (1–100 parts) is added to a solution containing polyethyleneimine (100 parts) and heated to promote reaction. Other methods of inducing crosslinking on already polymerized materials includes, but is not limited to, exposure to ionizing radiation, ultraviolet radiation, electron beams, radicals, and pyrolysis.

Polymers for binding free iron and heme-bound iron may be different, and their efficacies are assessed by different tests. For these reasons the two types of iron are discussed separately.

Heme-Bound Iron

One method of sequestering heme-bound iron would involve binding it to a polymer, rendering it unable to enter the mucosal cells. The structure of heme-bound iron is shown below.

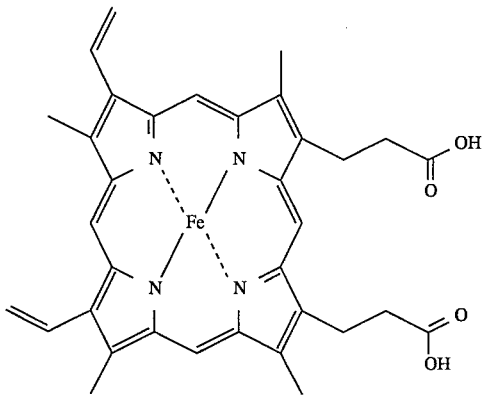

There are several logical ways to attach this molecule to a polymer, as described below.

1. Since in the small intestine the pH would typically be around 7, the two carboxylic acid groups will likely be ionized to form negatively charged $RCO_2^-$ groups. If the polymer contained positively charged groups the heme could be bound by its negatively charged groups through an ion-exchange mechanism. Examples of positively charged groups (at pH 7) would include primary, secondary, tertiary, and quaternary amines.

2. The iron atom itself is also available for binding, even though four of its six sites are taken up by the heme. In natural proteins, such as hemoglobin and cytochrome C, these sites are bound to by such ligands as the nitrogen group of histidine and the sulfur group of methionine. The polymer would thus incorporate one or more appropriate ligands to bind directly to the iron atom.

3. A polymer with a site that provided appropriate solvation for the various pans of the heme-iron would also effectively bind it. The heme unit incorporates a variety of organic functional groups that vary in their solvation requirements, from the various carboxylic acid groups which would be best solvated by polar, hydrogen bonding moieties to the allyl groups which would be better solvated by nonpolar, nonhydrogen-bonding moieties.

4. A preferred embodiment would include a polymer which combined two or more of these mechanisms in a single site or, alternatively, at separate sites.

In order to assess the potential of each candidate polymer a test was devised to quantitate the binding of the iron-heme unit to the polymer. This test involved stirring the polymer in a solution designed to mimic physiologic conditions. The amount of heme chosen corresponds to 10 mg of iron (a typical daily intake) and is dissolved in 1 L of fluid (the amount typically passing out of the small intestine in one day).

| Heme Iron Test Solution | |
|---|---|
| NaCl | 17.5 g |
| NaHCO$_3$ | 7.6 g |
| Hemin | 0.35 g dissolved in 5 mL 1M NaOH + 50 mL Water |
| Water | 3 L total volume |
| Acetic Acid | Adjust to pH 7 |

A specified amount of polymer was stirred in 100 mL of this solution for three hours. The pH was adjusted to 7.0 at both the start and end of this period. The solid was then filtered off and the amount of heme still present in the solution was determined spectroscopically. For any given polymer the amount of heme remaining in the solution is a function of the amount of polymer used in the test.

As shown in the following table, the amount of one preferred polymer, poly(ammoniumbutylacrylamide) (ABA), positively correlates with the percent heme remaining after filtration.

| Percent Heme Removed | Polymer Required | Daily Dose |
|---|---|---|
| 50 | 0.05 g | 0.5 g |
| 75 | 0.07 | 0.7 |
| 90 | 0.11 | 1.1 |
| 99 | 0.13 | 1.3 |
| 99.5 | 0.25 | 2.5 |
| 99.85 | 0.50 | 5.0 |

The daily dose column is an estimate of the dose required by a person who consumes 10 mg/day of heme iron. Thus to sequester 99% of the heme iron from this individual's diet he would have to take 1.3 g of polymer over the course of the day.

This test is extremely sensitive to the pH of the test solution, and care must be made to ensure that the pH is 7.0. As the pH is raised above pH 7, the binding drops off significantly. Further, at pH values below 7 (especially below 5.5) the heme is insoluble and precipitates. Thus the tests must be run carefully at pH 7.

In order to assess the relative binding ability of a variety of polymers, a few selected points were tested. The table below shows the data for a number of such polymers.

| | % Heme Remaining | | | |
|---|---|---|---|---|
| Polymer | 0.025 g | 0.05 g | 0.1 g | 0.2 g |
| Poly(ammoniumethylacrylamide) | — | 23 | 0–5.0 | <1 |
| Poly(ammoniumbutylacrylamide) | — | 50 | 19 | 1.3 |
| Poly(ammoniumhexylacrylamide) | — | 43–50 | 10 | 0.3 |
| Poly(dimethylaminopropylacrylamide) | — | 4 | <1 | <1 |
| Poly(dimethylaminopropylacrylamide.HCl) | — | 24 | 7 | <1 |
| Poly(ethyleneimine)"A" | 35–50 | 1–36 | <1 | <1 |
| Poly(diethylenetriaminemethacrylamide) | 15–39 | 0–17 | <1 | <1 |
| Poly(diethylaminopropylmethacrylamide) | 5–12 | 0–14 | <1 | <1 |

In order to combine the effects of ion exchange (binding method 1) with those of hydrophobicity (method 3) a series of copolymers was formed. In the first case a copolymer involving ammoniumethylacrylamide (AEA) and allylacrylamide (AA) was made with allylacrylamide portions ranging from 0% to 75%. As can be seen in the data below the higher the proportion of allylacrylamide in the polymer the poorer the binding is. In this case the added hydrophobicity did not increase the binding.

| Polymer | % Heme Remaining (0.2 g/100 mL) |
| --- | --- |
| 100% AEA | <2 |
| 75% AEA, 25% AA | ~5 |
| 50% AEA, 50% AA | ~35 |
| 25% AEA, 75% AA | ~50 |

Other polymers were also made to test the effects of hydrophobicity on binding. One set includes a comparison of an acrylamide polymer to the more hydrophobic methacrylamide equivalent. A second comparison from this set involves substitution of more hydrophobic ethyl groups for methyl groups. From these comparisons there is no clear trend concerning the effect of hydrophobicity on iron binding effectiveness.

| | % Heme Remaining | | | |
| --- | --- | --- | --- | --- |
| Polymer | 0.025 g | 0.05 g | 0.1 g | 0.2 g |
| Poly(dimethylaminopropylacrylamide) | — | 3 | <1 | <1 |
| Poly(dimethylaminopropylmethacrylamide) | 51 | 32 | <1 | <1 |
| Poly(diethylaminopropylmethacrylamide) | 8 | 2 | <1 | <1 |

Other comparisons involving hydrophobicity come from the following list of polymers:

| | % Heme Remaining | | |
| --- | --- | --- | --- |
| Polymer | 0.05 g | 0.1 g | 0.2 g |
| Poly(Ammoniumethylacrylamide) [=Poly(AEA)] | 23 | 0–5 | <1 |
| Copoly(AEA/polyethyleneglycol dimethacrylate). | 59 | 5 | — |
| Poly(Ammoniumhexylacrylamide) [=Poly(AHA)] | 43–50 | 10 | 0.3 |
| Copoly(AHA/dodecylacrylamide). | >50 | >50 | ~50 |
| Copoly(AHA/dehydroabeitylacrylamide/acrylamide) | — | — | >50 |

From these comparisons it is again shown that increased hydrophobicity does not improve iron binding. In order to make many of these comparisons some of the iron binding monomer was diluted with a nonpolar monomer. This dilution necessarily lowers the concentration of the primary monomer. Alternatively one can dilute the primary monomer with a hydrophilic monomer, thereby separating the effects of dilution from those of increased hydrophobicity.

| | % Heme Remaining | | |
| --- | --- | --- | --- |
| Polymer | 0.05 g | 0.1 g | 0.2 g |
| Poly(Ammoniumhexylacrylamide) [=Poly(AHA)] | 43–50 | 10 | 0.3 |
| Copoly(AHA/hydroxypropylacrylamide). | — | — | >50 |
| Copoly(AHA/acrylamide/vinylphosphonic acid) | >50 | — | >50 |

In this case the iron binding is much worse when the amine functionality is diluted with hydroxyl functionality, a substitution that is not expected to make the polymer significantly more hydrophobic. This result suggests that dilution of the primary monomer is a critical factor and that hydrophobic/hydrophilic effects may be secondary. Dilution with acrylamide and phosphonic acid functionality also impacts negatively on the binding properties. In this case the negative charge expected on the phosphonic acid groups may inhibit binding of the negatively charged heme groups.

A variety of other amine-containing polymers was tested for heme-iron binding. The data on these polymers is shown below. Clearly the polyvinylamine is very effective (among the best), while the other polymers are less so. It is evident from these and other data that all types of amines (primary, secondary, tertiary, quaternary, and heterocyclic) can be made to bond heme-bound iron.

| | | % Heme Remaining | | |
| --- | --- | --- | --- | --- |
| Polymer | Amine Functionality | 0.05 g | 0.1 g | 0.2 g |
| Polyvinylamine | R—NH2 | 4% | <1 | — |
| Poly(N-imidazolepropylacrylamide). |  | 16 | <1 | <1 |
| Poly(aminoethylpiperazine itaconate). | R—CONHCH$_2$CH$_2$N(CH$_2$CH$_2$)$_2$NH$_2$ or R—CON(CH$_2$CH$_2$)$_2$NCH$_2$CH$_2$NH$_2$ | 73 | — | 66 |
| Poly(PEH-acrylamide) | R—NH$_2$;R—NH—R | 78 | 72 | 59 |
| Poly(TAEA-acrylamide) | R—NH$_2$;R—NR$_2$ | 82 | 72 | 70 |
| Poly(Methacrylamidopropyltrimethylammoniumchloride) | R—N$^+$(CH$_3$)$_3$ | 57 | 12 | <1 |

A variety of polymers with functional groups designed to bond directly to the iron atom within the heme were tested with the results shown below. Two of these, poly(AEABMP) and poly(AEABPHA), also contained an amine functionality that could be positively charged under the conditions of the iron-binding test. Thus they are capable of both direct binding and binding by ion exchange. Those polymers without this capability (the first six in the table below) were less effective than those two with it.

| Polymer (0.2 g used) | Iron Binding Group(s) | % Heme Remaining |
| --- | --- | --- |
| Poly(cystinediacrylamide) | R—S—S—R | 92 |
| Poly(mercaptoethylacrylamide) | R—SH | 82 |
| Poly(cystaminediacrylamide) | R—S—S—R | >50 |
| Poly(N,N-methylcyanoethylacrylamide) | R—CN | 92 |
| Poly(IAHH) | R—CONHOH; R—CO2H | 83 |

| Polymer (0.2 g used) | Iron Binding Group(s) | % Heme Remaining |
|---|---|---|
| Poly(N-hydroxymethacrylamide) | R—CONHOH | 25 |
| Poly(AEABMP) | several | 10 |

Poly(AEABMP)

[Structure: R-C(=O)-NH-CH2CH2-N(-CH2CH2-C(=O)-OCH3)(-CH2CH2-C(=O)-OCH3)]

| | | |
|---|---|---|
| Poly(AEABPHA) | several | <1 |

Poly(AEABPHA)

[Structure: R-C(=O)-NH-CH2CH2-N(-CH2CH2-C(=O)-NHOH)(-CH2CH2-C(=O)-NHOH)]

It might be expected that the extent of crosslinking could impact the heme-binding characteristics of these polymers. Since heme is a relatively large molecule it might have difficulty finding its way into a tightly crosslinked polymer gel. Alternatively, a too loosely crosslinked network might not effectively hold a heme molecule because of the potentially greater loss in entropy in binding to it. A highly crosslinked network might have cavities just large enough for a heme to fit tightly in, just as substrates fit in enzymatic active sites, while a less crosslinked (or even uncrosslinked) polymer may have to wrap itself around a heme with a significant loss in its internal entropy.

In order to partially assess such hypotheses two identical polymers with different amounts of crosslinking were synthesized. Poly(ammoniumbutylacrylamide) was synthesized with either 5% or 10% methylenebisacrylamide as crosslinker. The data below show that little difference was observed. Either there is little effect of extent of crosslinking on heme-iron binding, or the effects take place primarily outside of the range tested.

| | % Heme Remaining | | |
|---|---|---|---|
| Crosslinking % | 0.05 g Polymer | 0.1 g Polymer | 0.2 g Polymer |
| 5 | 42 | 17 | <1 |
| 10 | 50 | 19 | 1.3 |

Two commercially available crosslinked polymeric materials that contain amine functionality are Questran® (cholestyramine; Bristol Laboratories) and Colestid® (Colestipol; Upjohn). The structures of these polymers are shown below.

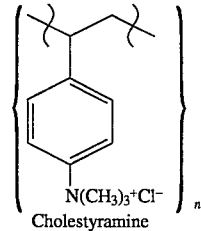
Cholestyramine

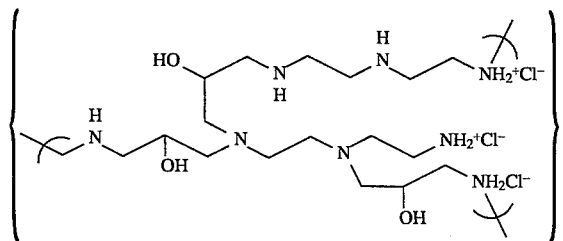
Typical Cholestipol Structure

Heme binding test results for these polymers are given in the following table. These products do demonstrate some heme-iron affinity, but they are not as effective as some of the polymers described above.

| Polymer (0.2 g) | % Heme Remaining |
|---|---|
| Cholestyramine | 53 |
| Colestipol | 60 |

Heme iron binding was also tested for two of the polymers in the presence of a variety of potential small intestine contents. A test solution was made up with the following ingredients:

| Ingredient | Amount |
|---|---|
| Hemin | 0.12 g Dissolved in 50 mL water |

-continued

| Ingredient | Amount |
|---|---|
|  | ∓mL 1N NaOH |
| Water | To 1 L Total Volume (~900 mL) |
| NaCl | 5.8 g |
| NaHCO₃ | 2.5 g |
| Crude Taurocholic Acid | 2.86 g |
| α-Alanine | 0.5 g |
| Arginine Hydrochloride | 0.5 g |
| Asparagine Monohydrate | 0.5 g |
| Aspartic Acid | 0.5 g |
| Citrulline | 0.5 g |
| Cystine | 0.5 g |
| β-3,4-Dihydroxyphenylalanine | 0.5 g |
| Glutamic Acid | 0.5 g |
| Glycine | 0.5 g |
| β-3,4-Dihydroxyphenylalanine | 0.5 g |
| Glutamic Acid | 0.5 g |
| Glycine | 0.5 g |
| Histidine Hydrochloride | 0.5 g |
| Isoleucine | 0.5 g |
| Leucine | 0.5 g |
| Lysine Hydrochloride | 0.5 g |
| Methionine | 0.5 g |
| Norleucine | 0.5 g |
| Norvaline | 0.5 g |
| Ornithine Hydrochloride | 0.5 g |
| Phenylalanine | 0.5 g |
| Proline | 0.5 g |
| Serine | 0.5 g |
| Threonine | 0.5 g |
| Tryptophan | 0.5 g |
| Tyrosine | 0.5 g |
| Valine | 0.5 g |

The pH was adjusted to 7.1 with acetic acid and some undissolved material was filtered off.

To this dark brown test solution was added 0.2 g of polymer. The solution was stirred 3 h, during which time the pH shifted to ~7.5 (and was not readjusted). The solid was filtered off and the iron content analyzed by atomic absorption spectroscopy at a commercial laboratory with the following results:

| Polymer | % Heme Remaining |
|---|---|
| Poly(Ammoniumhexylacrylamide) = Poly(AHA) | 55 |
| Poly(AEABPHA) | 66 |

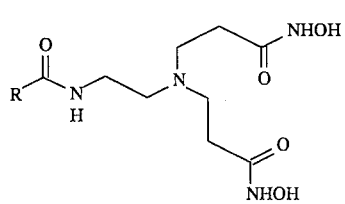

While it is evident that the polymers are not as effective as they are in the heme-iron only solution, they are still capable of binding a significant amount.

Free Iron

One effective method of sequestering free iron involves attachment of classic iron chelators to a crosslinked polymer backbone. Iron chelators are typically small molecules that have between two and six subunits that attach themselves directly to the iron atom. Desferal® (deferoxamine mesylate) is a good example. Good chelators contain such moieties as phenolates, enolic hydroxyls, ketones, aldehydes, carboxylates, phosphates and phosphonates, thiolates, sulfides and disulfides, hydroxamic acids and hydroxamates, amines, amides, and nitrones. The polymers can be designed such that the iron is chelated entirely by side chain groups:

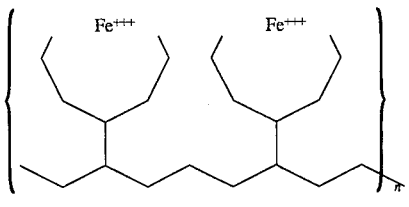

OR

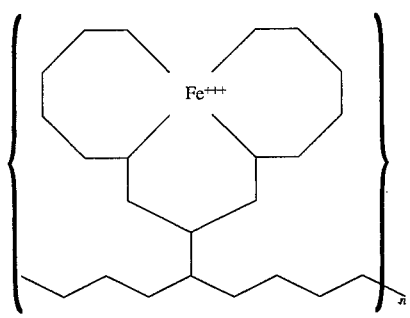

or such that it is chelated at least partially across the backbone:

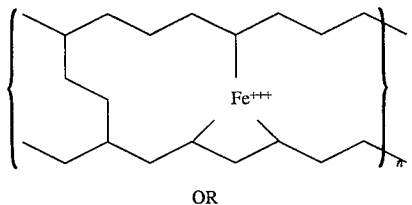

OR

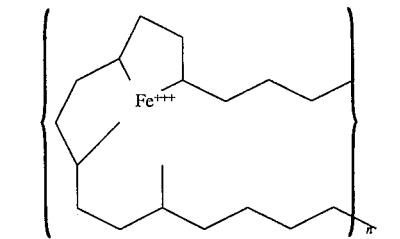

In order to assess the potential of each candidate polymer a test was devised to quantitate the binding of iron to the polymer. This test involved stirring the polymer in a solution designed to mimic physiologic conditions. The amount of iron chosen corresponds to ~9 mg of iron (a typical daily intake) and is dissolved in 1 L of fluid (the amount typically passing out of the small intestine in one day).

| Free Iron Test Solution | |
|---|---|
| NaCl | 20 g |
| FeCl₃.6 H₂O | 0.13 g |
| Citric Acid | 0.09 g |
| Water | 3 L Total Volume |
| NaOH | Adjust to pH 7 |

Results are shown below for a variety of polymers.

| Polymer | % Free Iron Remaining | | | | |
|---|---|---|---|---|---|
| | 0.001 g | 0.002 g | 0.003 g | 0.005 g | 0.01 g |
| Poly(ethyleneimine)"A" | 16 | 15 | 1.5–6 | 0–5 | 0 |
| Poly(ethyleneimine)"B" | — | 63 | 66 | 48 | — |
| Poly(ethyleneimine)"C" | — | 3.5 | 2.6 | <2 | — |
| Colestid | 85 | — | — | 33 | 30 |

| Polymer | % Free Iron Remaining | | | | |
|---|---|---|---|---|---|
| | 0.01 | 0.02 g | 0.03 g | 0.05 g | 0.1 g |
| Poly(diethylaminopropylmethacrylamide) | — | 32 | 1–23 | 0–11 | 1–39 |
| Poly(diethylenetriaminemethacrylamide) | — | — | 12 | 3 | 3 |
| Colestid | 30 | <2 | <2 | <2 | <2 |
| Poly(PEH-acrylamide) | 29 | 5 | 2 | <2 | <2 |
| Poly(TAEA-acrylamide) | — | — | 31 | 35 | 26 |
| Poly(dimethylaminopropylmethacrylamide) | 22 | 2 | <2 | <2 | <2 |

| Polymer | Iron Binding Group(s) | % Free Iron Remaining | | |
|---|---|---|---|---|
| | | 0.03 g | 0.05 g | 0.1 g |
| Poly(mercaptoethylacrylamide) | R—SH | — | — | 44 |
| Poly(IAHH) | R—CONHOH; R—CO2H | — | 57 | — |
| Poly(N-hydroxymethacrylamide) | R—CONHOH | 40 | 30 | 29 |
| Poly(N-methyl-N-hydroxymethacrylamide) | RCON(CH$_3$)OH | 6 | 6 | 8 |
| Poly(salicylic acrylamide) | R—C$_6$H$_3$(CO$_2$H)(OH) | ~100 at pH7 2 at pH11 | ~100 at pH7 5 at pH11 | ~100 at pH7 <2 at pH11 |
| Poly(3-hydroxytyracrylamide) | R—C$_6$H$_3$(OH)$_2$ | ~100 at pH7 4 at pH11 | 96 at pH7 4 at pH11 | 69 at pH7 <6 at pH11 |
| Poly(AEABMP) [R—C(O)NH—CH$_2$CH$_2$—N(CH$_2$CH$_2$C(O)OCH$_3$)$_2$] | several | — | 69 | — |
| Poly(AEABPHA) [R—C(O)NH—CH$_2$CH$_2$—N(CH$_2$CH$_2$C(O)NHOH)$_2$] | several | — | 25 | 7 using 0.2 g |
| Poly(cholinevinylphosphonate) | R—P(O)(O$^-$)(OH) | — | — | 82 |
| Poly(N-imidazolepropylacrylamide) | R—N(imidazole) | — | — | 19 |
| Poly(ammoniumhexylacrylamide) | R—NH$_2$ | 21 | 6 | 14 |
| Poly(vinylamine) | R—NH$_2$ | — | <2 | — |

| | | | | |
|---|---|---|---|---|
| Poly(diethylaminopropylmethacrylamide) | R—N(CH₂CH₃)₂ | 4 | 11 | 9 |
| Poly(dimethylaminopropylacrylamide-hydrochloride) | R—N(CH₃)₂ | 23 | 17 | 12 |
| Poly(dimethylaminopropylmethacrylamide hydrochloride) | R—N(CH₃)₂ | 47 | 41 | 34 after water washes 8 |
| Poly(methacrylamidopropyltrimethyl-ammonium chloride) | uncertain | 16 | 4 | 11 |

Clearly some of the polymers are more effective than others, with poly(vinylamine), poly(ethyleneimine), and poly(dimethylaminopropylmethacrylamide) being among the most effective.

METHODS

Heme-Iron Assay

The polymer to be tested is ground and sieved to −80/+200 mesh size unless it is already a fine powder, in which case it is used as is. A measured amount of the polymer (typically 0.05–0.2 g) is suspended in 100 mL of the heme test solution. The pH is adjusted to 7.0 using either acetic acid or 1 N NaOH as necessary. The mixture is then stirred for three h, at the end of which the pH is again adjusted to 7.0. The solid is then filtered off using Whatman #1 filter paper, and the liquid is examined spectroscopically.

Heme-bound iron has a broad absorption at ~340–380 nm. The absorption is determined at 365 nm and corrected for a baseline absorption, typically by subtracting the average of the absorbances at 280 and 450 nm.

$$A_{365} = A_{365}(\text{measured}) - (A_{280} + A_{450})/2 \quad (1)$$

The concentration of heme iron is then determined by comparison to a standard curve made using the starting solution and various dilutions thereof by plotting the relationship between corrected absorbance and the concentration of heme iron. The relationship is fit well by a straight line of the formula:

$$[\text{Heme Fe}] = 100\% \times [(0.189 \times A_{365}) + 0.001] \quad (2)$$

where the [Heme Fe] is the percent heme remaining by comparison to the starting heme solution.

Free Iron Assay

The free iron assay is identical to that used for heme iron except that the solutions are different and that after the polymer is filtered off the solution must be further worked up. To 50 mL of the filtered iron test solution is added 3 mL of 0.3% aqueous o-phenanthroline and 1 mL of 10% aqueous hydroxylamine hydrochloride. The solution is stirred, and the pH is brought to 3.5 using aqueous sodium citrate (250 g/L) or 0.1N sulfuric acid, then diluted to a final volume of 60 mL. The solution is stirred for 5 min and then allowed to sit for 20 h at room temperature. The absorbance is then read at 508 nm, with baseline points determined at 400 mm and 616 nm. The corrected absorbance at 508 nm is calculated by subtracting the average of the absorbances at 400 nm and 616 nm.

$$A_{508} A_{508}(\text{measured}) - (A_{400} + A_{616})/2 \quad (3)$$

The relationship between $A_{508}$ and the free iron concentration is not a single straight line over the entire range of interest. The relationship is linear over three ranges and the linear least squares fits were used to derive the equations below:

| Range Applicable ($A_{508}$) | Equation | |
|---|---|---|
| 0–0.008 | [Fe] = 333.3($A_{508}$) − 2.17 | (4) |
| 0.008–0.05 | [Fe] = 102.3($A_{508}$) − 0.30 | (5) |
| 0.05–1.1 | [Fe] = 92.3($A_{508}$) + 0.63 | (6) | where [Fe] is the % of free iron remaining compared to the original solution. Values of [Fe] below 2% are reported as "<2"% due to uncertainty in this range.

Examples of Polymer Syntheses

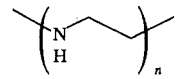

Poly(ethyleneimine)"A". Polyethyleneimine (50 g of a 50% aqueous solution; Scientific Polymer Products) was dissolved in water (100 mL). Epichlorohydrin (4.6 mL) was added dropwise. The solution was heated to 55° C. for 4 h, after which it had gelled. The gel was removed, blended with water (1 L) and the solid was filtered off, the rinse repeated once with water and twice with isopropanol, and the resulting gel was dried in a vacuum oven to yield 26.3 g of a rubbery solid.

Poly(ethyleneimine)"B" and Poly(ethyleneimine)"C" were made in a similar manner, except using 9.2 and 2.3 mL of epichlorohydrin, respectively.

Poly(methylmethacrylate-co-divinylbenzene). Methylmethacrylate (50 g) and divinylbenzene (5 g) and azobisisobutyronitrile (AIBN; 1.0 g) were dissolved in isopropanol (500 mL) and heated to reflux for 18 h under a nitrogen atmosphere. The solid white precipitate was filtered off, timed once in acetone (collected by centrifugation), once in water (collected by filtration) and dried in a vacuum oven to yield 19.4 g.

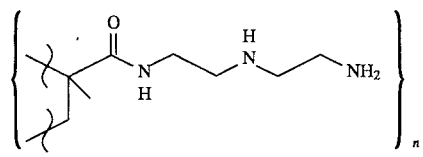

OR

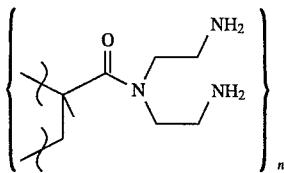

Poly(diethylenetriaminemethacrylamide). Poly(methylmethacrylate-co-divinylbenzene) (20 g) was suspended in diethylenetriamine (200 mL) and heated to reflux under a nitrogen atmosphere for 18 h. The solid was collected by filtration, resuspended in water (500 mL), filtered off, resuspended in water (500 mL), collected by filtration, rinsed briefly in isopropanol, and dried in a vacuum oven to yield 18.0 g.

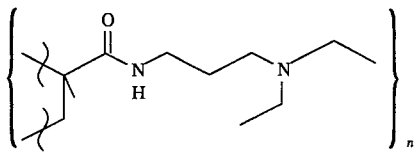

Poly(diethylaminopropylmethacrylamide). Poly(methylmethacrylate-co-divinylbenzene) (20 g) was suspended in diethylaminopropylamine (200 mL) and heated to reflux under a nitrogen atmosphere for 18 h. The solid was collected by filtration, resuspended in water (500 mL), filtered off, resuspended in water (500 mL), collected by filtration, rinsed briefly in isopropanol, and dried in a vacuum oven to yield 8.2 g.

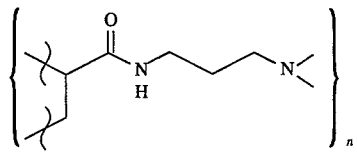

Poly(dimethylaminopropylacrylamide). Dimethylaminopropylacrylamide (10 g) and methylenebisacrylamide (1.1 g) were dissolved in water (50 mL) in a 100 mL three neck flask. The solution was stirred under nitrogen for 10 minutes. Potassium persulfate (0.3 g) and sodium metabisulfite (0.3 g) were each dissolved in water (2–3 mL) and then mixed. After a few seconds this solution was added to the monomer solution, still under nitrogen. A gel formed immediately and was allowed to sit overnight. The gel was removed and blended with isopropanol (500 mL). The solid was filtered off and timed three times with acetone. The solid white powder was filtered off and dried in a vacuum oven to yield 6.1 g.

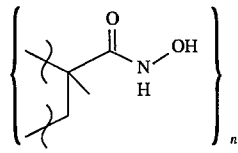

Poly(N-hydroxymethacrylamide). Poly(methylmethacrylate) (5.5 g; ground and sieved to −80/+200 mesh size) was put into a 500 mL three neck flask fitted with a thermometer and reflux condenser. Hydroxylamine hydrochloride (14 g) was dissolved in boiling methanol (72 mL) and added to the polymer while still hot. Potassium hydroxide (17 g) was dissolved in boiling methanol (43 mL) and also added to the polymer solution while hot. Methanol (50 mL) was added and the mixture was refluxed under a nitrogen atmosphere for 24 h. After cooling, water was added to a total volume of 500 mL. The solid was collected by centrifugation and resuspended in water (800 mL). The pH of the solution was adjusted to 7.0 with acetic acid and the solid collected by centrifugation. After resuspension and centrifugation from water (800 mL), the solid was rinsed three times with isopropanol (1 L, 300 mL, 300 mL, respectively) the solid was collected by filtration and dried in a vacuum oven to yield 2.6 g.

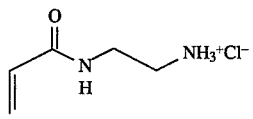

Ammoniumethylacrylamide (AEA). Acryloyl chloride (45.75 g) was dissolved in tetrahydrofuran (THF; 400 mL) in a 1 L flask. The solution was cooled to 8° C. in an ice bath and ethylenediamine (28.85 g) in THF (400 mL) was added dropwise, keeping the temperature at 8°–10° C. After addition the solution was stirred for 5 min and the solid was collected by filtration, washed three times in THF (50 mL), and dried in a vacuum oven to yield 74 g.

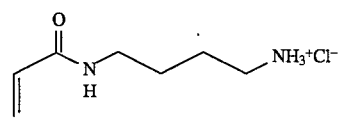

Ammoniumbutylacrylamide (ABA). Acryloyl chloride (45.26 g) was dissolved in THF (400 mL) in a 1 L flask. The solution was cooled to 10° C. in an ice bath and butanediamine (42.3 g) in THF (100 mL) was added dropwise. After addition the solid was collected by filtration, washed three times in THF (50 mL), and dried in a vacuum oven to yield 80.9 g.

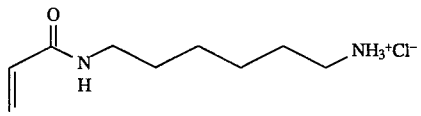

Ammoniumhexylacrylamide (AHA). Hexanediamine (30 g) dissolved in THF (100 mL) was added dropwise to acryloyl chloride (23.4 g) dissolved in THF (300 mL) in an ice bath, keeping the temperature below 15° C. The solid that formed was filtered off, rinsed twice with THF, and dried in a vacuum oven to yield 48.5 g.

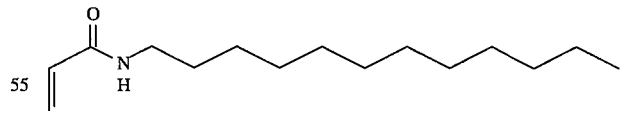

Dodecylacrylamide. Acryloyl chloride (19 g) was dissolved in THF (200 mL) in a 1 L flask and placed in an ice bath. A solution containing dodecylamine (37.1 g), triethylamine (20.2 g) and THF (300 mL) was added dropwise, maintaining the temperature at 5°–15° C. After addition the solution was stirred for 5 min and the solid was filtered off and discarded. The solvent was removed in vacuo from the mother liquor and methanol (50 mL) was added to the residue. After stirring, water (200 mL) was added and crystals formed. Additional water (200 mL) was added, the solution was stirred for 30 min, and the solid was filtered off. The solid was vacuum dried at room temperature to yield 40.3 g.

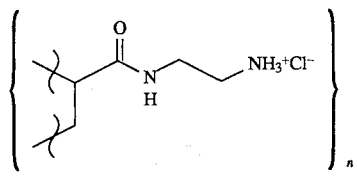

Poly(AEA). AEA (20 g) and methylenebisacrylamide (2.2 g) were dissolved in warm water (32° C.; 100 mL). Potassium persulfate (0.2 g) was added with stirring. After 5 minutes potassium metabisulfite (0.2) was added with continued stirring. Within 5 minutes curds of polymer had formed. The solution was allowed to sit for 4 h and was then broken up and stirred in water (700 mL) for 1 h followed by filtration. The solid was then resuspended and filtered twice more with water (500 mL) and three times with isopropanol (500 mL). The solid was then vacuum dried to yield 11.0 g.

Copoly(AEA/allyl acrylamide). Several copolymers were formed by substituting allylacrylamide for some portion of the AEA in the above procedure. Portions used were 20 g AEA/0 g allylacrylamide, 15 g AEA/5 g allylacrylamide, 10 g AEA/10 g allylacrylamide, and 5 g AEA/15 g allylacrylamide. Yields were 11.0, 10.8, 10.8, and 10.6 g respectively.

Poly(AEA/polyethyleneglycol dimethacrylate). AEA (10 g), polyethylene glycol dimethacrylate (10 g; mw=600), and 0.32 g AIBN were suspended in dimethylsulfoxide (50 mL). The mixture was slowly heated under a nitrogen atmosphere. Gel formation started before all AEA was dissolved. The gel was kept at 90° C. for 60 min and then cooled under nitrogen. After sitting overnight the gel was removed, blended with isopropanol (500 mL), and the solid was collected by filtration. The solid was rinsed three times with water (500 mL), three times with isopropanol (500 mL) and dried in a vacuum oven to yield 13.45 g.

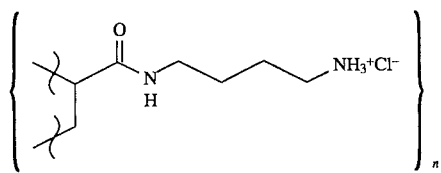

Poly(ABA). ABA (27.0 g), methylenebisacrylamide (3.0 g), water (250 mL), and methanol (100 mL) were mixed together and warmed (35° C.) to dissolve. A small mount of insolubles were filtered off. Potassium persulfate (0.3 g) and potassium metabisulfite (0.3 g) were each dissolved in water (a few mL) and added to the monomer solution. After 4 h the mixture was blended with isopropanol (500 mL) twice and dried in a vacuum oven to yield 21.4 g. The solid (21.4 g) was suspended three times in water (2 L), and collected by filtration each time. The solid was then rinsed in isopropanol (1 L) and dried in a vacuum oven to yield 17.2 g.

Alternatively, to yield a 5% crosslinked polymer instead of the 10% crosslinked polymer made above the same procedure was carried out using 28.5 g of monomer and 1.5 g of crosslinker. The final yield was 15.9 g.

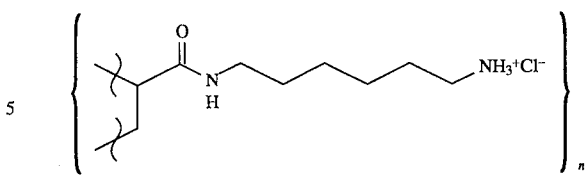

Poly(AHA), AHA (40 g) and methylenebisacrylamide (4.4 g) were dissolved in a warm mixture containing water (200 mL) and methanol (200 mL). Potassium persulfate (0.4 g) and potassium metabisulfite (0.4 g) were each dissolved in water (3 mL). After dissolving they were mixed together and within a few seconds added to the warm monomer solution. Curds of polymer formed immediately and within 2 minutes the solution had gelled. The solution was allowed to sit overnight and was then stirred in water (1.5 L) for 1 h followed by filtration. The solid was rinsed twice with water, three times with methanol, and three times with isopropanol before being dried in a vacuum oven to yield 24.0 g.

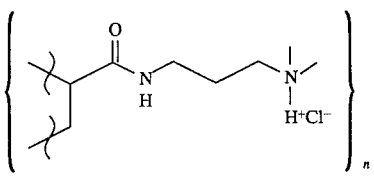

Poly(dimethylaminopropylacrylamide hydrochloride). Dimethylaminopropyl-acrylamide (20.10 g) was dissolved in water (100 mL) and neutralized with concentrated HCl to pH 6.95. Methylenebisacrylamide (2.2 g) and water (100 mL) were added and warmed (34° C.) to dissolve. Potassium persulfate (0.2 g) and potassium metabisulfite (0.2 g) were added with stirring. After gelation, the solution was allowed to sit for 6 h, was blended with isopropanol (600 mL) three times, and dried in a vacuum oven to yield 14.47 g.

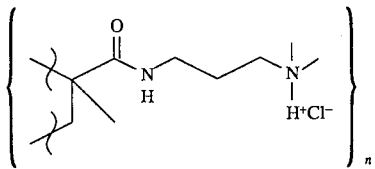

Poly(dimethylaminopropylmethacrylamide hydrochloride).

Dimethylaminopropylmethacrylamide (20.0 g) was dissolved in water (100 mL) and neutralized with concentrated HCl to pH 6.94. Methylenebisacrylamide (2.2 g) was added and the solution was warmed (39° C.) to dissolve. Potassium persulfate (0.3 g) and potassium metabisulfite (0.3 g) were added with stirring under a nitrogen atmosphere. After gelation, the solution was allowed to sit overnight, was blended with isopropanol (500 mL) twice, and dried in a vacuum oven to yield 27.65 g. Some of the solid (3.2 g; sieved to −80/+200 mesh size) was stirred in water (100 mL) for 50 min, additional water (100 mL) was added and the solution stirred for 36 min. The solid was collected by centrifugation, resuspended in water (400 mL), stirred 150 min, and again collected by centrifugation. The solid was finally resuspended in water (500 mL), stirred 90 min, and collected by filtration. The solid was dried in a vacuum oven to yield 0.28 g.

Copoly(AHA/hydroxypropylacrylamide). AHA (10 g), hydroxypropylacrylamide (10 g), methylenebisacrylamide (2.2 g), and AIBN (0.25 g) were suspended in DMSO (50 mL) under a nitrogen atmosphere. The mixture was slowly heated. At 39° C. the mixture was homogeneous. The solution gelled just below 60° C. The heat of polymerization took the temperature up to 115° C. The solution was allowed to slowly cool to room temperature under a nitrogen atmosphere and allowed to sit for 3 h. The gel was removed, blended twice with isopropanol, and the solid was collected by filtration. The solid was rinsed three times in water, three times in isopropanol, and dried in a vacuum oven to yield 15.5 g.

Copoly(AHA/dodecylacrylamide). AHA (4 g), dodecylacrylamide (4 g), methylenebisacrylamide (0.9 g), and 0.25 g AIBN were dissolved in dimethylsulfoxide (25 mL). The mixture was slowly heated under a nitrogen atmosphere. Before reaching 90° C. the solution began to polymerize, driving the temperature up to 110° C. The gel was allowed to cool and sit overnight under nitrogen. The solid was removed, blended with of isopropanol (500 mL), and collected by filtration. The solid was resuspended and then filtered from isopropanol once, from water three times, and finally from isopropanol three times. The solid was dried in a vacuum oven to yield 5.3 g.

Copoly(AHA/acrylamide/vinylphosphonic acid). AHA (5 g), acrylamide (5 g), vinylphosphonic acid (5.9 g of 90% solution), methylenebisacrylamide (1.5 g), and AIBN (0.35 g) were dissolved in dimethylsulfoxide (35 mL). The mixture was slowly heated under a nitrogen atmosphere. At 50° C. the solution gelled, with the heat of polymerization heating it to 110° C. The gel was allowed to cool and sit for 4 h under nitrogen. The solid was removed, blended three times with methanol, three times with water, three times with isopropanol, and dried in a vacuum oven to yield 9.2 g.

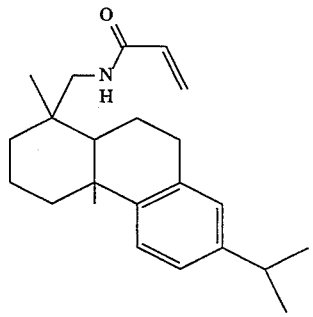

N-Dehydroabeitylacrylamide. Dehydroabeitylamine (15 g of Technical Grade) and triethylamine (5.85 g) dissolved in THF (100 mL) was added dropwise to acryloyl chloride (5.25 g) dissolved in THF (100 mL) in an ice bath. The white solid (triethylaminehydrochloride) was filtered off and discarded. The solvent was evaporated in vacuo to leave an oil. The oil was dissolved in ethylacetate (300 mL), rinsed once with water (500 mL) saturated with NaCl (whose pH became 2.3), rinsed once with 5% NaHCO₃ saturated with NaCl (200 mL; pH became 7.8), and finally was dried over MgSO₄ before evaporation of the ethylacetate in vacuo to leave 16 g of solid.

Copoly(AHA/dehydroabeitylacrylamide/acrylamide). AHA (3 g), N-dehydroabeitylacrylamide (3 g), acrylamide (3 g), methylenebisacrylamide (1.0 g), and AIBN (0.25 g) were dissolved in dimethylsulfoxide (25 mL). The mixture was slowly heated under a nitrogen atmosphere. Below 90° C. the solution gelled, with the heat of polymerization heating it to 115° C. The gel was allowed to cool under nitrogen. The solid was removed, blended three times with isopropanol (500 mL), twice with water (1 L), three times with methanol, and dried in a vacuum oven to yield 6.5 g.

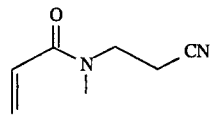

N-Methyl-N-β-cyanoethylacrylamide. N-Methyl-βb-cyanoethylamine (N-Methyl-β-alaninenitrile; 30 g) and triethylamine (36.4 g) were dissolved in THF (100 mL). This solution was added dropwise to acryloyl chloride (32.6 g) dissolved in THF (200 mL) in an ice bath. The solid was filtered off and the solvent removed in vacuo to leave 37.8 g.

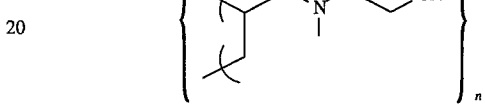

Poly(N-Methyl-N-β-cyanoethylacrylamide). N,N-Methylcyanoethylacrylamide (10 g), methylenebisacrylamide (1.1 g), and AIBN (0.3 g) were dissolved in dimethylsulfoxide (50 mL). The mixture was slowly heated under a nitrogen atmosphere. At ~100° C. the solution polymerized, sending the temperature up to 115° C. The solution was allowed to cool and sit overnight. The gel was removed, blended gently four times in isopropanol, and dried in a vacuum oven to yield 10.65 g.

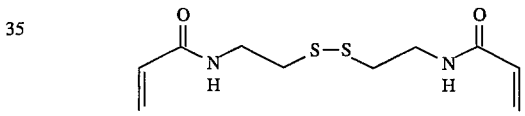

Cystaminediacrylamide. Cystamine dihydrochloride (20 g) and potassium carbonate (61.4 g) were dissolved in water (150 mL) and placed in an ice bath. Acryloyl chloride (24.2 g) was added dropwise, with solid formation on addition. The solid was filtered off, rinsed twice with water, and dried in a vacuum oven to yield 16.6 g.

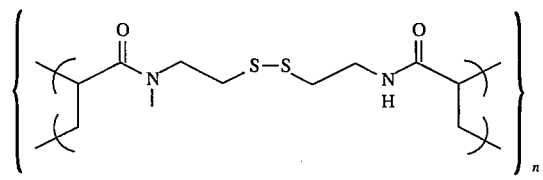

Poly(cystaminediacrylamide). Cystaminediacrylamide (15 g) and methylenebisacrylamide (1.65 g) were dissolved in a mixture of methanol (150 mL) and water (50 mL). The mixture was heated to reflux allowing near complete dissolution of the solid. Potassium persulfate (0.3 g) and potassium metabisulfite (0.3 g) were each dissolved in water (2–3 mL). After dissolving they were mixed together and within a few seconds added to the hot monomer solution. Polymer formation was evident within 1 minute. The solution was refluxed for 1 h, cooled to room temperature, and the solid was filtered off. The solid was rinsed twice in water, twice in methanol, twice in isopropanol, and dried in a vacuum oven to yield 7.0 g.

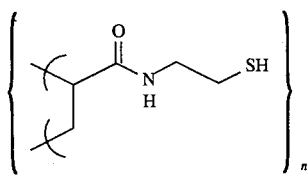

Poly(mercaptoethylacrylamide).

Method A. Poly(cystaminediacrylamide) (0.8 g; ground and sieved to −80/+200 mesh size) was suspended in a mixture of methanol (75 mL), water (50 mL), and mercaptoethanol (10 mL). The mixture was stirred overnight under a nitrogen atmosphere. The solid was filtered off, rinsed four times in methanol, three times in isopropanol, and dried in a vacuum oven to yield 0.65 g of pink solid.

Method B. Poly(cystaminediacrylamide) (1.25 g; unsieved) was suspended in water (100 mL). Sodium borohydride (2.25 g) was added under a nitrogen atmosphere. The solution was stirred overnight and the solid was filtered off, rinsed three times in water, three times in methanol, and dried in a vacuum oven to yield 0.84 g of pink solid.

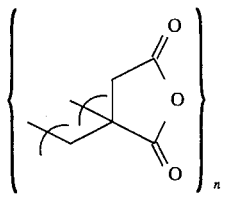

Poly(itaconic anhydride). Itaconic anhydride (22.4 g), ethyleneglycoldimethacrylate (13.3 g), and toluene (500 mL) were mixed in a 1 L flask and heated to 80° C. Azobisisobutryonitrile (2 g) was dissolved in toluene (50 mL) and added dropwise over a two hour period to the monomer solution. The solution was stirred for one additional hour at 80° C., cooled to room temperature, and the solid polymer was filtered off. The solid was rinsed with THF, stirred in THF for 30 minutes followed by filtration, and dried in a vacuum oven to yield 37 g.

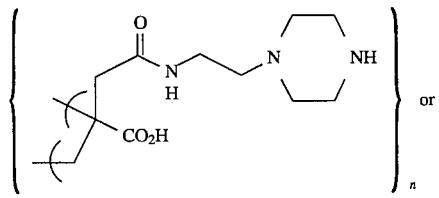

or

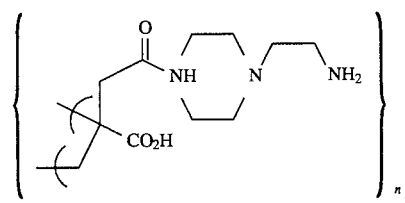

Poly(aminoethylpiperazine itaconate). Poly(itaconic anhydride) (5 g) was suspended in acetone (100 mL) to which was added 1-(2-aminoethyl)piperazine (26 g). The solution was stirred for 1 h and the solids were filtered off, rinsed twice in acetone, once in water, and suspended in water (150 mL) where the pH was read to be 7.2. The solids were again filtered off, rinsed once in water, once in 1 N HCl (pH of the slurry=0.75), and twice in water (pH <3 for both). The solids were suspended in water (300 mL) and 1 N NaOH was added to pH 7.0. The solids were rinsed three additional times in water, three times in methanol, once in isopropanol, and dried in a vacuum oven to yield 5.8 g.

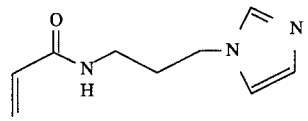

N-Imidazolepropylacrylamide. 1-(3-aminopropyl)imidazole (25 g) dissolved in THF (100 mL) was added dropwise to acryloyl chloride (18.1 g) dissolved in THF (200 mL) in an ice bath. The solid that formed was filtered off and dried in a vacuum oven to yield 39.2 g of a semisolid. This crude material was polymerized without further purification.

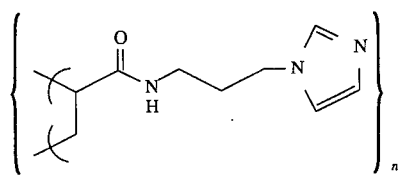

Poly(N-imidazolepropylacrylamide). Crude N-imidazolepropylacrylamide (17.7 g) and methylenebisacrylamide (2.0 g) were dissolved in water (100 mL). Potassium persulfate (0.4 g) and potassium metabisulfite (0.4 g) were each dissolved in water (3 mL). After dissolving they were mixed together and within a few seconds added to the monomer solution under a nitrogen atmosphere. In ~10 minutes the solution gelled lightly and was left overnight. The gel was blended four times with isopropanol (500 mL) and dried in a vacuum oven to yield 11.8 g. The solid was resuspended in water (500 mL), stirred 30 minutes, and refiltered twice more. The solid was rinsed twice in methanol, three times in isopropanol, and dried in a vacuum oven to yield 6.7 g.

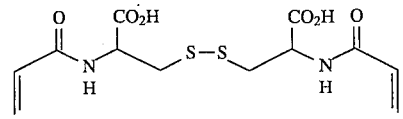

Cystinediacrylamide. Cystine (50 g) and potassium carbonate (174 g) were nearly dissolved in water (400 mL) and placed in an ice bath. Acryloyl chloride (57 g) was added dropwise over a 1 h period, keeping the temperature below 15° C. The mixture was allowed to warm to room temperature and the pH was measured to be 7.9. Concentrated HCl was added until the pH reached 1.2. The water was removed in vacuo and THF (500 mL) was added and stirred for 20 minutes. The solid was filtered off and discarded. The THF was removed in vacuo to leave a thick liquid. The liquid was suspended in acetone (1 L) and stirred for 30 minutes. Any solid remaining was filtered off and discarded. The acetone was removed in vacuo to yield 78.3 g.

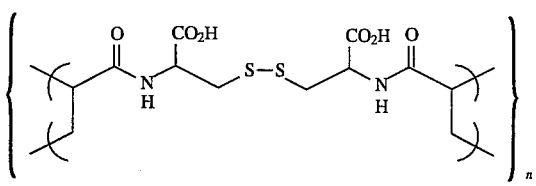

Poly(cystinediacrylamide). Cystineacrylamide (75.5 g) and methylenebisacrylamide (7 g) were dissolved in a mixture containing water (300 mL) and methanol (200 mL). Potassium persulfate (1.0 g) and potassium metabisulfite (1.0 g) were each added with stirring. No change was observed in 15 min. The addition of initiators was repeated dissolving each in a few mL of water prior to addition. Still no sign of polymerization. AIBN (1.0 g) was added and the solution heated to reflux under a nitrogen atmosphere. Before reaching reflux a copious white solid was formed. The heating was stopped and the water (2 L) and stirred 1 h. The solids were collected by filtration, resuspended in methanol (2 L), filtered off, and dried in a vacuum oven to yield 76.7 g.

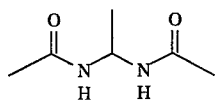

Ethylidenebisacetamide. Acetamide (118 g), acetaldehyde (44.06 g), copper acetate (0.2 g), and water (300 mL) were placed in a 1 L three neck flask fitted with condenser, thermometer, and mechanical stirrer. Concentrated HCl (34 mL) was added and the mixture was heated to 45°–50° C. with stirring for 24 h. The water was then removed in vacuo to leave a thick sludge which formed crystals on cooling to 5° C. Acetone (200 mL) was added and stirred for a few minutes after which the solid was filtered off and discarded. The acetone was cooled to 0° C. and solid was filtered off. This solid was timed in acetone (500 mL) and air dried 18 h to yield 31.5 g.

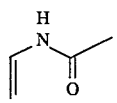

Vinylacetamide. Ethylidenebisacetamide (31.05 g), calcium carbonate (2 g) and celite 541 (2 g) were placed in a 500 mL three neck flask fitted with a thermometer, a mechanical stirrer, and a distilling head atop a vigroux column. The mixture was vacuum distilled at 35 mm Hg by heating the pot to 180°–225° C. Only a single fraction was collected (10.8 g) which contained a large portion of acetamide in addition to the product. This solid product was dissolved in isopropanol (30 mL) to form the crude solution used for polymerization.

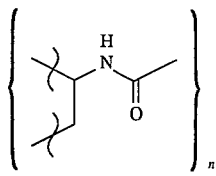

Poly(vinylacetamide). Crude vinylacetamide solution (15 mL), divinylbenzene (1 g, technical grade, 55% pure, mixed isomers), and AIBN (0.3 g) were mixed and heated to reflux under a nitrogen atmosphere for 90 min, forming a solid precipitate. The solution was cooled, isopropanol (50 mL) was added, and the solid was collected by centrifugation. The solid was timed twice in isopropanol, once in water, and dried in a vacuum oven to yield 0.8 g.

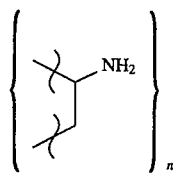

Poly(vinylamine). Poly(vinylacetamide) (0.79 g) was placed in a 100 mL one neck flask containing water (25 mL) and conc. HCl (25 mL). The mixture was refluxed for 5 days, the solid was filtered off, rinsed once in water, twice in isopropanol, and dried in a vacuum oven to yield 0.77 g. The product of this reaction was suspended in NaOH (46 g) and water (46 g) and heated to boiling (~140° C.). The temperature was reduced and maintained at ~100° C. for 2 h. Water (100 mL) was added and the solid collected by filtration. After rinsing once in water the solid was suspended in water (500 mL) and adjusted to pH 5 with acetic acid. The solid was again filtered off, rinsed with water, then isopropanol, and dried in a vacuum oven to yield 0.51 g.

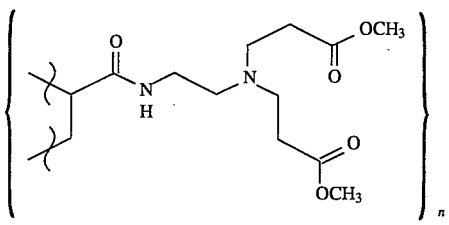

Poly(AEABMP). Poly(AEA) (19.12 g; made without any water washes) was suspended in methanol (100 mL). A second solution containing KOH (7.2 g) and methanol (25 mL) was partially added (~⅓) until the apparent pH stabilized at 9. Water (200 mL) was added, and additional KOH/methanol solution was added until the pH reached 12. After stirring the mixture overnight the solid was filtered off, rinsed with water, suspended in water (300 mL), stirred 1 h, filtered off, and dried in a vacuum oven to yield 11.2 g of deprotonated poly(AEA).

This solid (11.2 g) was placed in a 250 mL flask containing methanol (75 mL). Methyl acrylate (25.8 g) was added and the mixture stirred for 21 days. The solid was then filtered off and dried in a vacuum oven to yield 20.2 g.

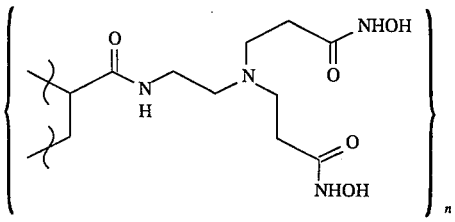

Poly(AEABPHA). Hydroxylamine hydrochloride (22.2 g) was dissolved in methanol (110 mL) in a 500 mL flask. A solution containing KOH (30.7 g) and methanol (70 mL) was added and the solution cooled to 28° C. after a slight exotherm to 52° C. The cooled solution was filtered, the solid washed with methanol, and the liquid fraction combined with poly(AEABMP) (20.2 g). After stirring the mixture for 4 days, acetic acid (30 g) was added and the mixture stirred for 1 h. The solid was filtered off, timed with water, resuspended in water, stirred 1 h, and finally filtered off. The solid was dried in a vacuum oven to yield 9.55 g.

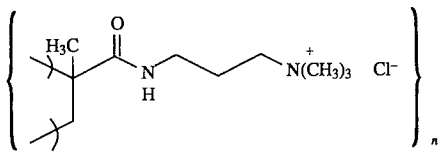

Poly(Methacrylamidopropyltrimethylammonium chloride). Methacrylamidopropyltrimethylammonium chloride (38 mL of 50% aqueous solution) and methylenebismethacrylamide (2.2 g) were stirred in a beaker at room temperature. Methanol (10 mL) was added and the solution was warmed to 40° C. to fully dissolve the bisacrylamide. Potassium persulfate (0.4 g) was added and the solution stirred for 2 min. Potassium metabisulfite (0.4 g) was added and stirring was continued. After 5 min the solution was put under a nitrogen atmosphere. After 20 min the solution contained significant precipitate and the solution was allowed to sit overnight. The solid was washed three times with isopropanol and collected by filtration. The solid was then suspended in water (500 mL) and stirred for several hours before being collected by centrifugation. The solid was again washed with water and collected by filtration. The solid was then dried in a vacuum oven to yield 21.96 g.

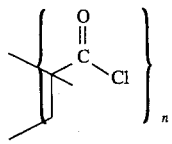

Poly(methacryloyl chloride). Methacryloyl chloride (20 mL), divinyl benzene (4 mL of 80% purity), AIBN (0.4 g), and THF (150 mL) were stirred at 60° C. under a nitrogen atmosphere for 18 h. The solution was cooled and the solid was filtered off, rinsed in THF, then acetone, and dried in a vacuum oven to yield 8.1 g.

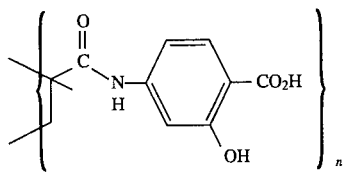

Poly(salicylic acrylamide). 4-Aminosalicylic acid (10 g), triethylamine (2 mL), acetone (50 mL) and poly(methacryloyl chloride) (0.88 g) were stirred together for 18 hours. The solid was filtered off, rinsed with water, stirred in water (500 mL) for 30 minutes, filtered off, stirred in water a second time, stirred in isopropanol, and dried in a vacuum oven to yield 0.84 g.

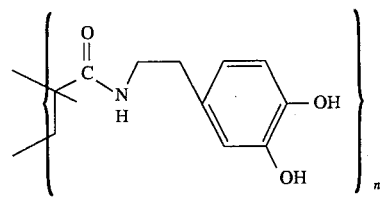

Poly(3-hydroxytyracrylamide). 3-Hydroxytyramine hydrochloride (2.0 g), triethylamine (5 mL), acetone (100 mL) and poly(methacryloyl chloride) (1.0 g) were stirred together for 4 days. Water (100 mL) was added and the solution stirred 30 minutes. The solid was filtered off, rinsed with water, stirred in water (500 mL) for 30 minutes, filtered off, stirred in two more times, stirred in methanol (500 mL) three times, and dried in a vacuum oven to yield 1.12 g.

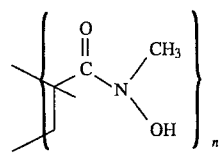

Poly(N-methyl-N-hydroxymethacrylamide). Methylhydroxylamine hydrochloride (8.35 g), poly(methacryloyl chloride) (5.0 g), and 1 M NaOH (100 mL) were mixed together and the pH adjusted to 7.7 with 1 M HCl. The mixture was blended for 3 minutes at high speed in a blender and then stirred for 18 hours. The solid was filtered off, stirred in water (500 mL) for 10 minutes, filtered off, rinsed twice in water, once in isopropanol, and dried in a vacuum oven to yield 4.5 g.

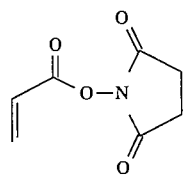

NHS-acrylate. N-Hydroxysuccinimide (NHS, 157.5 g) was dissolved in chloroform (2300 mL) in a 5 L flask. The solution was cooled to 0° C. and acryloyl chloride (132 g) was added dropwise, keeping T<2° C. After addition was complete, the solution was stirred for 1.5 h, rinsed with water (1100 mL) in a separatory funnel and dried over anhydrous sodium sulfate. The solvent was removed under vacuum and a small amount of ethyl acetate was added to the residue. This mixture was poured into hexane (200 mL) with stirring. The solution was heated to reflux, adding more ethyl acetate (400 mL). The insoluble NHS was filtered off, hexane (1 L) was added, the solution was heated to reflux, ethyl acetate (400 mL) was added, and the solution allowed to cool to <10° C. The solid was then filtered off and dried in a vacuum oven to yield 125.9 g. A second crop of 80 g was subsequently collected by further cooling.

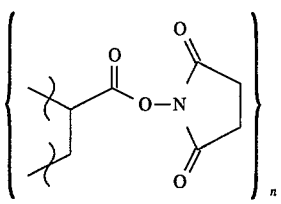

Poly(NHS-acrylate). NHS-acrylate (28.5 g), methylenebisacrylamide (1.5 g) and tetrahydrofuran (500 mL) were mixed in a 1 L flask and heated to 50° C. under a nitrogen atmosphere. Azobisisobutyronitrile (0.2 g) was added, the solution was stirred for 1 h, filtered to remove excess N-hydroxysuccinimide, and heated to 50° C. for 4.5 h under a nitrogen atmosphere. The solution was then cooled and the solid was filtered off, rinsed in tetrahydrofuran, and dried in a vacuum oven to yield 16.1 g.

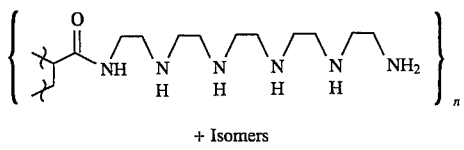

+ Isomers

Poly(PEH-acrylamide). Poly(NHS-acrylate) (5.0 g) was suspended in a solution containing water (100 mL) and pentaethylene hexamine (30 mL) which had been adjusted to pH 10 with concentrated HCl. After four days of stirring, the solid was filtered off and resuspended in water (500 mL). The mixture was stirred for 4 h, the solid was filtered off, and the wash repeated. The solid was then timed briefly with water twice, isopropanol once, and dried in a vacuum oven to yield 4.7 g.

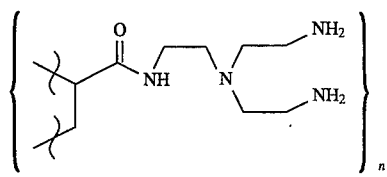

Poly(TAEA-acrylamide). Poly(NHS-acrylate) (4.4 g) was suspended in a solution containing water (100 mL) and tris(2-aminoethyl)amine (30 mL) which had been adjusted to pH 9 with concentrated HCl. After four days of stirring, the solid was filtered off and resuspended in water (500 mL). The mixture was stirred for 4 h, the solid was filtered off, and the wash repeated. The solid was then timed briefly with water twice, isopropanol once, and dried in a vacuum oven to yield 3.4 g.

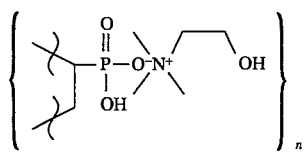

Poly(cholinevinylphosphonate). Vinylphosphonic acid (52.3 g) and methylenebisacrylamide (5.2 g) were mixed, heated gently to dissolve, sealed in a glass reaction kettle under vacuum, and exposed to uv light for 3 days. The resulting solid was removed, blended twice in isopropanol (600 mL), collected by filtration, and dried in a vacuum oven ,yielding 25.4 g. This solid was then ground and suspended in water (400 mL). Choline bicarbonate was added until the pH reached 6.5. The solution was stirred for 1 h, after which the solid was filtered off with the addition of ethanol to collapse the gel. The solid was rinsed twice with ethanol (500 mL) and dried in a vacuum oven to yield 23.8 g.

Use

The polymers of the invention are intended to decrease the uptake of dietary iron, after oral administration. The polymers may be administered as a composition which includes ingredients, such as other therapeutically active substances, inert ingredients, and carrier compounds. The components of the composition must be compatible, meaning that the components must be capable of being commingled with the polymer and with each other in a manner such that there is no interaction which would substantially reduce during use the composition's efficacy for decreasing the absorption of dietary iron.

The composition formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing up to 10% by weight of the active compound, soft and hard gelatin capsules, packaged powders, and the like. Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrrolidone, cellulose, water syrup, methyl cellulose, methylhydroxybenzoates, propylhydroxybenzoates, propylhydroxybenzoates, talc, and other compounds as are well known to those skilled in the pharmaceutical arts.

The term "patient" used herein is taken to mean any mammalian patient to which iron-binding polymers may be administered. Patients specifically intended for treatment with the method of the invention include humans, as well as nonhuman primates, sheep, horses, cattle, goats, pigs, dogs, cats, rabbits, guinea pigs, hamsters, gerbils, rats and mice.

The polymers would be taken orally, and would then mix with the dietary constituents in the digestive track and inhibit absorption of iron. The polymers would be acting by binding the iron and reducing its bioavailability. The polymers would be crosslinked to form small particles that would be confined to the digestive track and would not be available to the blood or other extraluminal fluids or organs. As the dietary constituents passed through the individual, so too would the polymer, until eventually it was excreted in the feces.

In order to prevent dietary uptake one must prevent both free iron and heme-bound iron from entering the mucosal cells. To do this, in one embodiment the therapeutic polymer would be administered to remove from 70–95% of the available dietary iron, leaving a small but adequate amount of iron available to meet the minimal ongoing iron needs of patients, as well as the iron requirements of the patients' intestinal flora. Alternatively, enough polymer may be administered to sequester all (99+%) of the dietary iron, and the patient would also take an iron supplement at a time when no sequesterant is present. This latter approach would allow better control since it may be difficult for patients to balance their sequesterant dose with their dietary iron intake to leave an appropriate amount of non-sequestered iron. Sequestration of dietary iron by traditional iron-binding substances, such as deferoxamine, would not be effective in this application as they would be unable to prevent uptake of heme-bound iron from the lumen.

What is claimed is:

1. A method of reducing dietary iron absorption in a patient in need thereof comprising orally administering to said patient a therapeutically effective amount of at least one polymer that binds dietary iron in vivo, said polymer being non-toxic and stable once ingested.

2. The method of claim 1 wherein said polymer reduces dietary iron absorption by at least about 70%.

3. The method of claim 1 wherein said polymer reduces dietary iron absorption by at least about 95%.

4. The method of claim 1 wherein said polymer reduces dietary heme iron absorption by at least about 70%.

5. The method of claim 1 wherein said polymer reduces dietary free iron absorption by at least about 70%.

6. The method of claim 1 wherein said polymer comprises primary, secondary, tertiary, or quaternary amines.

7. The method of claim 6 wherein said amines comprise —NR3+, where each R group, independently, is H or a lower alkyl or aryl group.

8. The method of claim 1 wherein said polymer comprises iron chelating groups.

9. The method of claim 8 wherein said iron chelating group comprises a phenolate, enolic hydroxyl, ketone, aldehyde, carboxylate, phosphate, phosphonate, thiolate, sulfide, disulfide, hydroxamic acid, hydroxamate, amine, amide, nitrone, ether, thiol, hydroxyl, sulfonate, nitrile, or isonitrile group, or combination thereof.

10. The method of claim 1 wherein said polymer is crosslinked.

11. The method of claim 1 wherein said polymer is characterized by a repeating group having the formula

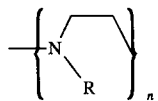 (1)

or a copolymer thereof, wherein n is an integer, and each R, independently, is H, OH, or a lower alkyl or aryl group.

12. The method of claim 1 wherein said polymer is characterized by a repeating group having the formula

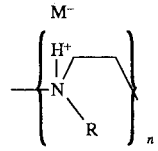 (2)

or a copolymer thereof, wherein n is an integer, each R, independently, is H, OH, or a lower alkyl or aryl group, and each M⁻ is an exchangeable negatively charged counterion.

13. The method of claim 1 wherein said polymer is characterized by a repeating group having the formula

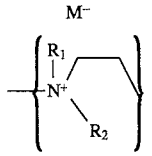 (3)

or a copolymer thereof, wherein n is an integer, and each $R_1$ and $R_2$, independently, is H, OH, or a lower alkyl or aryl group, and each M⁻ is an exchangeable negatively charged counterion.

14. The method of claim 1 wherein said polymer is characterized by a repeating group having the formula

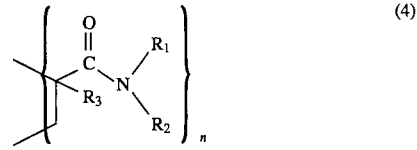 (4)

or a copolymer thereof, wherein n is an integer, $R_3$ is either H or a lower alkyl group, and each $R_1$ and $R_2$, independently, is H, OH, a lower alkyl or aryl group, or $(CH_2CH_2NH)_mH$, wherein m is an integer from 1 to 10,000.

15. The method of claim 1 wherein said polymer is characterized by a repeating group having the formula

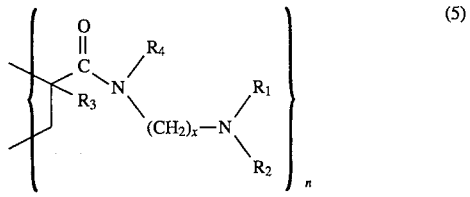 (5)

or a copolymer thereof, wherein n is an integer, $R_3$ is either H or a lower alkyl group, each $R_1$, $R_2$, and $R_4$, independently, is H, OH, or a lower alkyl or aryl group, and x is an integer from 1 to 25.

16. The method of claim 1 wherein said polymer is characterized by a repeating group having the formula

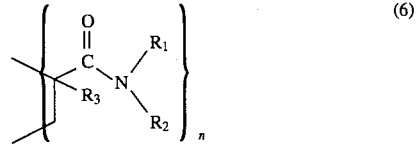 (6)

or a copolymer thereof, wherein n is an integer, $R_3$ is either H or a lower alkyl group, each $R_1$ and $R_2$, independently, is H, OH, a lower alkyl or aryl group, or an iron binding ligand.

17. The method of claim 1 wherein said polymer is characterized by a repeating group having the formula

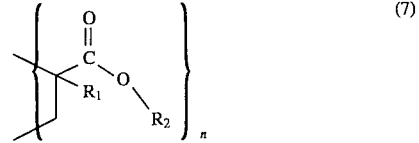 (7)

or a copolymer thereof, wherein n is an integer, $R_1$ is either H or a lower alkyl group, $R_2$ is H, OH, a lower alkyl or aryl group, or an iron binding ligand.

18. The method of claim 1 wherein said polymer is characterized by a repeating group having the formula

 (8)

or a copolymer thereof, wherein n is an integer, each $R_1$ and $R_2$, independently, is H, an alkyl group containing 1 to 20 carbon atoms, or an aryl group containing 1 to 12 atoms.

19. The method of claim 1 wherein said polymer is characterized by a repeating group having the formula

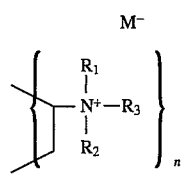
(9)
or a copolymer thereof, wherein n is an integer, each $R_1$, $R_2$ and $R_3$, independently, is H, an alkyl group containing 1 to 20 carbon atoms, or an aryl group containing 1 to 12 atoms, and each $M^-$ is an exchangeable negatively charged counterion.
* * * * *